United States Patent [19]

Kvitrud et al.

[11] Patent Number: 5,785,178

[45] Date of Patent: Jul. 28, 1998

[54] PACKAGED PHOTOCURABLE COMPOSITION

[75] Inventors: James R. Kvitrud, White Bear Lake; Thomas W. Martin, Little Canada; Steven E. Shimota, Woodbury, all of Minn.

[73] Assignee: Minnesota Mining and Manufacturing Co., St. Paul, Minn.

[21] Appl. No.: 743,646

[22] Filed: Nov. 4, 1996

[51] Int. Cl.[6] .......................... B65D 90/02; B65D 25/54; B67D 5/38
[52] U.S. Cl. .................. 206/459.1; 215/379; 220/665; 222/156
[58] Field of Search ................... 206/459.1, 527, 206/63.5; 215/379, 365, 366; 220/663, 662, 665; 222/156, 207, 206, 51, 154, 215

[56] References Cited

U.S. PATENT DOCUMENTS

| | | | |
|---|---|---|---|
| 1,085,560 | 1/1914 | Flynn | 215/366 |
| 1,206,792 | 12/1916 | Aumuller | 215/366 |
| 2,043,860 | 6/1936 | Morgan | 99/163 |
| 2,293,475 | 8/1942 | Serra | 215/366 |
| 2,294,473 | 9/1942 | Makeley | 206/459 |
| 2,631,499 | 3/1953 | Riley | 88/109 |
| 2,643,982 | 6/1953 | Riley | 260/32.8 |
| 3,291,621 | 12/1966 | Hagedron | 106/52 |
| 3,655,985 | 4/1972 | Brown et al. | 206/459.1 |
| 4,227,615 | 10/1980 | Flick | 215/379 |
| 4,785,953 | 11/1988 | Buchholz et al. | 215/365 |
| 4,822,280 | 4/1989 | Rider | 206/63.5 |
| 4,978,007 | 12/1990 | Jacobs et al. | 206/469 |
| 5,122,057 | 6/1992 | Discko, Jr. | 433/90 |
| 5,172,809 | 12/1992 | Jacobs et al. | 206/63.5 |
| 5,234,688 | 8/1993 | Gaffar | 206/524.1 |
| 5,246,145 | 9/1993 | Leoncavallo et al. | 222/153 |
| 5,328,058 | 7/1994 | Leoncavallo et al. | 222/153 |

OTHER PUBLICATIONS

Advertisement for EFD dispenser, *Medical Product Manufacturing News*, Mar. 1994.

*Primary Examiner*—Paul T. Sewell
*Assistant Examiner*—Anthony Stashick
*Attorney, Agent, or Firm*—James D. Christoff

[57] ABSTRACT

A packaged composition includes a vial having wall portions defining a chamber and a photocurable material in the chamber. The wall portions transmit less than about 1.0% of actinic radiation, and at least one of the wall portions transmits light having wavelengths in at least part of the visible spectrum. In certain embodiments of the invention, the wall portions are flexible and the photocurable material is dispensed from the chamber through an outlet when the wall portions are squeezed together. In other embodiments of the invention, an element is floating in the photocurable material in the chamber to facilitate determination of the amount of photocurable material remaining in the chamber.

14 Claims, 2 Drawing Sheets

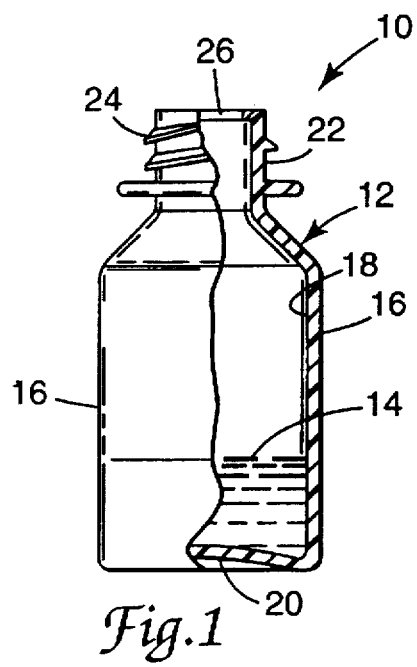
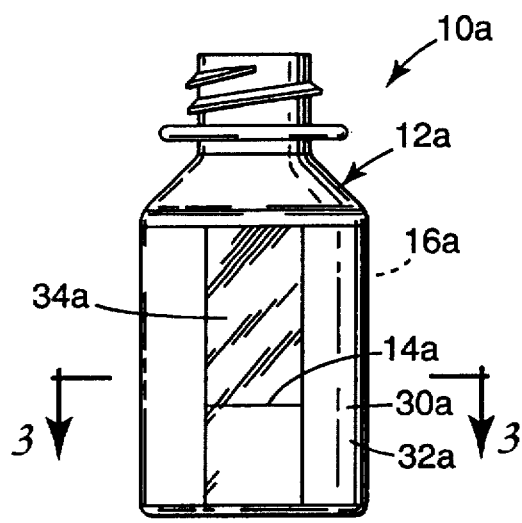
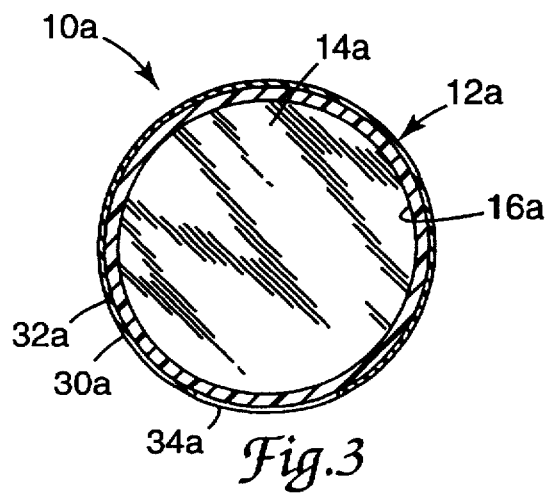

5,785,178

PACKAGED PHOTOCURABLE COMPOSITION

BACKGROUND OF THE INVENTION

1. Field of the Invention

This invention relates to a packaged composition that includes a squeezable vial having a chamber that receives a quantity of photocurable material.

2. Description of the Related Art

Many liquid and semi-liquid compositions used in small quantities in household, commercial or industrial applications are sold in small vials such as dropper bottles, squeezable applicators and the like. Typically, such vials are relatively inexpensive and are disposed of once their contents have been exhausted or have not been used by a specified expiration date.

Many small vials used for containing and dispensing liquid and semi-liquid compositions are made of a flexible polymeric material. To dispense the composition, opposed wall portions of the vial are squeezed together by finger pressure to expel the composition through an outlet. The flexible wall portions are an advantage in that the user can control to some degree the amount and flow rate of the composition that is dispensed. In addition, the flexible wall portions are less likely to break if the vial is unintentionally dropped or subjected to other kinds of abuse in comparison to vials made of glass or other rigid material.

Squeezable polymeric vials have been long used for various medical and dental preparations. Examples include eye and ear medications, suntan and sunscreen compositions, body lotions, cosmetics, topical ointments and insect repellents. Commercial and industrial applications include compositions for film developing and other photographic applications, adhesives (such as cyanoacrylates), lubricants and the like.

Many squeezable vials are made of a polymeric material that is sufficiently transparent or translucent so that the user may visually estimate the amount of composition remaining in the vial. In some instances, the transparent or translucent material helps the user ascertain whether or not the composition has degraded. For example, the user may be able to determine whether or not an adhesive has unduly hardened or thickened by shaking the vial and observing the fluidity of the contents through the polymeric wall portions.

Some compositions that are contained in squeezable vials are curable upon exposure to light having wavelengths in the visible spectrum. Examples of photocurable compositions include certain dental (including orthodontic) adhesives and primers, dental luting cements and other dental preparations such as sealants and crown build-up material. In the past, vials containing such photocurable compositions have included a sufficient amount of pigment such as carbon black that absorbs light and blocks substantially all of the light from entering the chamber in the vial and unduly curing the contained composition.

Unfortunately, opaque squeezable containers are not entirely satisfactory, since the user cannot visibly ascertain the amount of composition remaining in the vial. In addition, some vials and especially certain vials containing dental compositions are relatively small and contain only a small amount of composition. With such vials, it is difficult to determine the amount of remaining composition by lifting the vial and estimating its weight, since the ratio of the weight of the vial to the weight of the composition is relatively large.

SUMMARY OF THE INVENTION

The disadvantages noted above with respect to conventional squeezable vials have been overcome by the present invention. In one aspect, the invention concerns a packaged composition that comprises a vial having wall portions defining a chamber and an outlet communicating with the chamber. The wall portions are made of a polymeric material having a flexural modulus less than about 200,000 kg/cm$^2$. A photocurable material is in the chamber and is dispensed through the outlet when the wall portions are squeezed together. The wall portions transmit less than about 1.0% of actinic radiation, and at least one of the wall portions transmit at least part of the visible spectrum.

The invention in another aspect concerns a packaged composition that comprises a vial having wall portions defining a chamber and an outlet communicating with the chamber. A photocurable liquid is in the chamber. The wall portions transmit less than about 1.0% of actinic radiation, and at least one of the wall portions transmits at least part of the visible spectrum. An element floats in the liquid. The element is visible through the at least one wall portion transmitting at least part of the visible spectrum in order to indicate the level of liquid in the chamber.

The present invention provides an inexpensive, efficient solution to the problem of accurately determining the liquid level of a contained composition in conventional, squeezable vials that are opaque. The present invention enables the user to quickly ascertain the amount of composition remaining in the vial by visual inspection. As a consequence, additional vials can be obtained if necessary in order to ensure that there is sufficient composition available to complete the task at hand.

These and other aspects of the present invention are described in more detail in the paragraphs that follow and in the accompanying drawings.

BRIEF DESCRIPTION OF THE DRAWINGS

FIG. 1 is a side elevational view of a packaged composition in accordance with one embodiment of the invention, and wherein a vial is cut away in partial section in order to illustrate a quantity of photocurable composition contained therein;

FIG. 2 is a side elevational view of a packaged composition according to another embodiment of the invention;

FIG. 3 is a horizontal enlarge sectional view taken along lines 3—3 of FIG. 2;

DETAILED DESCRIPTION OF THE PREFERRED EMBODIMENTS

Figure 4:
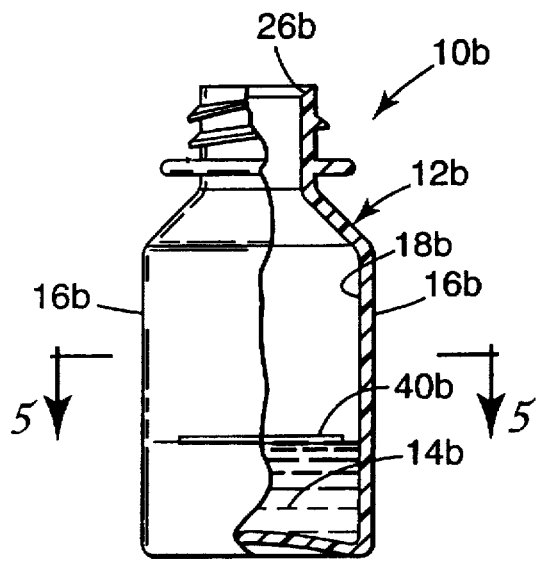
FIG. 4 is side elevational view somewhat similar to FIG. 1 but in accordance with yet other embodiment of the invention.

A packaged composition according to one embodiment of the invention is illustrated in FIG. 1 and is designated by the numeral 10. The packaged composition 10 broadly includes a vial 12 and a photocurable material 14.

The vial 12 includes a series of upright wall portions 16 that define a generally cylindrical internal chamber 18 that receives the photocurable material 14. The bottom of the chamber 18 is defined by a bottom wall 20 that is interconnected to the upright wall portions 16.

The vial 12 also includes a neck portion 22 that is connected to the upright wall portions 16. The neck portion 22 includes an external threaded section 24 as well as an uppermost outlet 26.

The threaded section 24 receives a threaded closure cap having a dispensing opening and a closure for selectively covering the opening. A suitable closure cap is described in U.S. Pat. No. 5,328,058 which is incorporated by reference herein. However, other types of dispensing outlets and closure caps may also be utilized.

The vial 12 including the wall portions 16, the bottom wall 20 and the neck portion 22 are preferably integrally molded and made of a polymeric material. The polymeric material has a flexural modulus that is preferably less than about 200,000 kg/cm², more preferably less than about 20,000 kg/cm² and most preferably less than about 2,000 kg/cm². The wall portions 16 have a thickness (in horizontal reference planes viewing FIG. 1) that is preferably in the range of about 0.005 inch to about 0.1 inch (0.12 mm to 2.5 mm), more preferably in the range of about 0.01 inch to about 0.06 inch (0.25 mm to 1.5 mm) and most preferably in the range of about 0.01 inch to about 0.03 inch (0.25 mm to 0.75 mm).

The flexural modulus and thickness of the upright wall portions 16 are selected to enable opposed sections of the wall portions 16 to be readily squeezed together by finger pressure. As the opposed sections are squeezed together, free space in the chamber 18 is reduced and the photocurable material 14 in the chamber 18 is expelled through the outlet 26. The polymeric material has sufficient memory to enable the sections to recover from deformation and fully return to their original shape once the finger pressure is released so that the upright wall portions 16 re-assume their normal, generally cylindrical configuration.

Suitable polymeric materials for making the vial 12 include blow-molded low density polyethylenes ("LDPE") such as no. 5104 from Chevron. However, as alternatives, the vial 12 may be made out of other polymeric materials such as high density polyethylene ("HDPE"), polyvinyl chloride ("PVC"), poly(ethylene glycol-co-cyclohexane-1, 4-dimethanol terephthalate) ("PETG") or poly(ethylene terephthalate) ("PET"). The selected polymeric material should be compatible with the photocurable material 14 and not unduly degrade over an extended period of time.

The photocurable material 14 is a liquid or semi-liquid material that is curable upon exposure to selective actinic radiation, i.e., wavelengths of light (electromagnetic radiation) that effect curing in the material. Examples of photocurable material include dental (including orthodontic) adhesives and primers, luting cements, crown build-up material and sealants. Such materials have a photoinitiator (such as camphorquinone ("CPQ")) that initiates curing when exposed to actinic radiation. The photocurable material 14 may also be a non-dental material such as a medical preparation or a composition intended for household, commercial or industrial application, and may be opaque or relatively clear.

The vial 12 including the wall portions 16, the bottom wall 20 and the neck portion 22 preferably transmit less than about 1.0% of actinic radiation, more preferably less than about 0.5% of actinic radiation and most preferably less than about 0.2% of actinic radiation. As a result, the photocurable material 14 may remain in the chamber 18 for an extended period of time without unduly curing.

However, at least one of the upright wall portions 16 transmits light having wavelengths in at least part of the visible spectrum. This allows the user to see the photocurable material 14 through such upright wall portion(s) 16 so that the level of material 14 in the chamber 18 can be determined.

As an example, if the photocurable material 14 is a dental adhesive that includes a photoinitiator that comprises CPQ, the adhesive will begin to cure when exposed to light having wavelengths near about 470 nm. Preferably, the wall material of the vial containing such dental adhesive blocks the passage of most of the light having such wavelengths, as well as light having other wavelengths that are substantially similar. In such example, the wall portions preferably transmit less than about 1.0% of light having wavelengths in the range of about 400 nm to about 500 nm.

Various colorants such as pigments and/or dyes are useful for making the polymeric material absorb selective wavelengths of electromagnetic radiation. The amount of colorant necessary per unit of polymeric material to provide the desired protection will vary depending on various factors, such as the particular colorant selected, the thickness of the wall sections of the vial, the wavelength of light to be absorbed and the capacity of the non-colorant-treated polymeric material to absorb the light of the wavelength to be filtered.

A suitable colorant for the dental adhesive mentioned above is no. 70344 HCP from Teknor Color Company. The vial 12 may be made, for example, by mixing 6% by weight of the colorant with 94% of a LDPE "carrier" resin. The resultant mixture is then mixed with LDPE (such as no. 5104, from Chevron) at a "let-down" ratio of 5:1 (i.e., a ratio of five parts LDPE to one part carrier and colorant mixture by volume). Preferably, the carrier resin has a slightly lower melting temperature than the melting temperature of the remaining quantity of LDPE to facilitate mixing. A suitable carrier resin is Yukalon Lm-31 from Mitsubishi Petro.

A packaged composition 10a according to another embodiment of the invention is illustrated in FIGS. 2 and 3. The packaged composition 10a includes a vial 12a and a photocurable material 14a. Preferably, the vial 12a and the photocurable material 14a are the same or closely similar to the vial 12 and the photocurable material 14 respectively described above except for the differences noted in the paragraphs that follow, and as a consequence a detailed description of such items need not be repeated.

As shown in FIGS. 2 and 3, upright wall portions 16a of the vial 12a include a label 30a that extends around the circumference of the vial 12a and also substantially along the entire height of the upright wall portions 16a. The label 30a includes a first section 32a that is opaque or substantially opaque to the passage of light, especially light having wavelengths in the visible spectrum. The label 30a also includes a second section 34a that is transparent or translucent to light having wavelengths in the visible spectrum. Both of the sections 32a, 34a block the passage of all or at least a substantial portion of actinic radiation.

The label 30a may be made of any of a number of suitable materials, including polymeric film stock. Examples of suitable material include polyethylene labels from Flexcon Company, Inc. Optionally, the label 30a could be made of a coextruded polyethylene film wherein the first section 32a is made of an extruded mixture of polyethylene and black, white or other pigment, while the second section 34a is simultaneously extruded from a stream of polyethylene without such pigment. As another alternative, the label 30a may be made of transparent or translucent polyethylene film, and a quantity of ink is applied to the first section 32a to render it opaque to the passage of light in the visible wavelength spectrum. As another option, the second section 34a is eliminated and the photocurable material 14a is viewed through the gap between adjacent end portions of the label 30a.

Although not shown in the drawings, one side of the label 30a is coated with a pressure sensitive adhesive to firmly secure the label 30a to the upright wall portions 16a. An example of a suitable adhesive is a 0.0008 inch (0.04 mm) thick layer of permanent acrylic adhesive (no. V-157 from Flexcon). Preferably, adjacent end sections of the label 30a overlap in order to reduce the likelihood of flagging and assure that the end portions of the label 30a tightly adhere to the wall portions 16a.

The label 30a enhances the visibility of the level of the photocurable material 14a in the vial 12a when the user is viewing the photocurable material 14a through the second section 34a. Advantageously, since the first section 32a also hinders transmission of actinic radiation there is less likelihood that an undue amount of actinic radiation will reach the photocurable material 14a.

Figure 5:
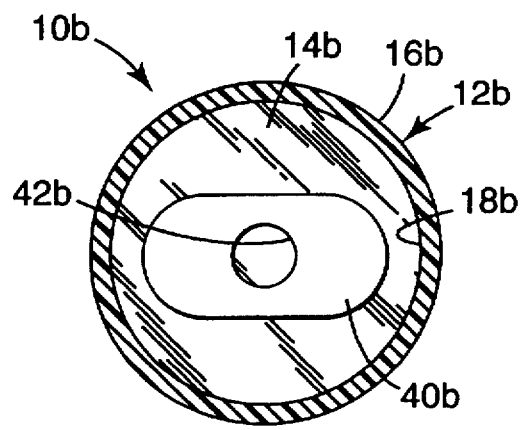
FIG. 5 is a horizontal enlarge sectional view taken along lines 5—5 of FIG. 4.

Another embodiment of the invention is shown in FIGS. 4 and 5, wherein a package composition 10b includes a vial 12b and a photocurable material 14b. Both the vial 12b and the photocurable material 14b are preferably identical to the vial 12 and photocurable material described above, except for the differences set out below.

The vial 12b includes a float or element 40b that is received in the chamber 18b. The element 40b has a density less than the density of the photocurable material 14b, and as a result floats in the photocurable material 14b. The element 40b is visible through the upright wall portions 16b that transmit light in the visible wavelength spectrum and thereby enhances the user's ability to determine the level or amount of photocurable material 14b in the chamber 18b.

Preferably, the element 40b has dimensions along two axes that are smaller than the dimensions of outlet 26b so that the element 40b can be inserted into the chamber 18b through the outlet 26b after the vial 12b is manufactured. As an example, if the chamber 18b of the vial 12b has an internal diameter of 0.64 inch (1.6 cm), the element 40b has overall dimensions of 0.25×0.50 inch (6.4×13 mm) and a thickness of 0.06 inch (1.5 mm). As illustrated in FIG. 5, the element 40b preferably has an overall generally oval-shaped configuration in plan view.

Preferably, the element 40b has a thickness in the range of about 0.01 inch to 0.06 inch (0.25 mm to 1.5 mm). The flat shape and relatively small thickness of the 40b helps the 40b return to a horizontal orientation after the vial 12b has been inverted and then returned to the vertical orientation that is depicted in FIGS. 4 and 5. Moreover, the flat shape of the element 40b tends to cast a more distinct shadow than a float having, for example, a spherical shape and as a result is relatively easy to see through the wall portions 16b.

Preferably, the element 40b has a central hole 42b. The hole 42b improves fluid flow of the photocurable material 14b to the outlet 26b when the vial 12b is inverted during a dispensing operation. The element 40b is made of a material that is inert to the photocurable material 14b; a suitable material that is inert to many photocurable materials is polyethylene. The element 40b could be a liquid, a semi-liquid (gel or paste) or (most preferably) a solid material that is either hollow or not hollow.

Figure 6:
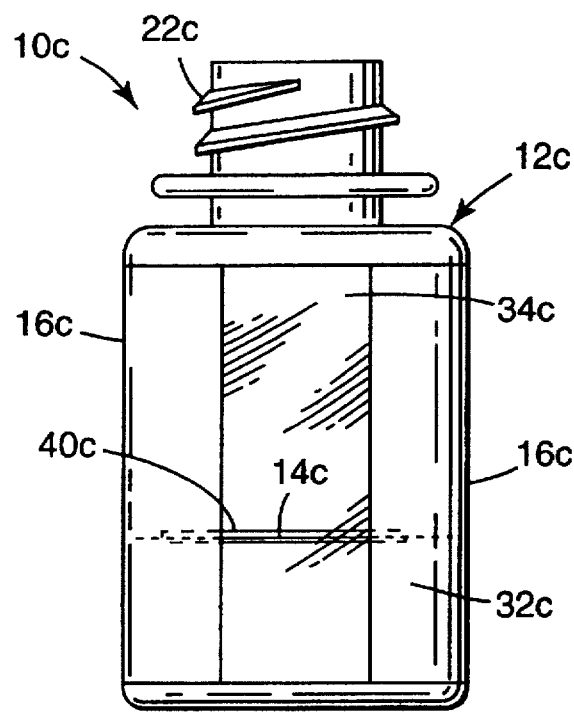
FIG. 6 is a view somewhat similar to FIG. 5 except in accordance with still another embodiment of the invention.

Another embodiment of the invention is depicted in FIG. 6, wherein a package composition 10c includes a vial 12c and a photocurable material 14c, the latter of which is identical to the photocurable material 14 described above.

The vial 12c has a generally oval-shaped overall configuration in plan view, and a chamber within the vial 12c has a generally oval-shaped overall configuration in plan view as well. A threaded neck portion 22c of the vial 12c is identical to the neck portion 22, and may receive a cap of the type described above or a cap of a different configuration.

The vial 12c has upright wall portions 16c surrounding the chamber 18c. The upright wall portions 16c include a first section 32c that is preferably covered or at least substantially covered with a coating. Preferably, the coating is opaque or at least substantially opaque to the passage of light in the visible spectrum as well as in the actinic spectrum. An example of a suitable coating is ink that is applied by a pad printing or silk screening technique and preceded by flame treatment to ensure good adhesion of the ink to the vial 12c.

The upright wall portions 16c also include a second section 34c that lacks or substantially lacks the coating that is applied to the first section 32c. As a consequence, the second section 34c transmits more light in the visible spectrum than the light transmitted through the first section 32c.

Additionally, the vial 12c includes a float or element 40c that is received in the chamber. The element 40c is somewhat similar to the element 40b, but is longer in length in order to better match the shape of the chamber in plan view. The first section 32c, the second section 34c and the element 40c help the user determine the level of photocurable material 14c in the chamber.

Those skilled in the art may recognize that a variety of alternatives are possible to the presently preferred embodiments described in detail above. For example, the shape of the vial may have another configuration, such as a configuration similar to squeezable tubes or squeezable containers of other configurations, and could be made of polymeric materials and colorants different than the materials and colorants set out above. Furthermore, the outlet could be open or covered with a sponge, brush, swab or other type of applicator. Accordingly, the scope of the invention should not be deemed limited by the specific descriptions mentioned above, but only by a fair reading of the claims that follow along with their equivalents.

We claim:

1. A packaged composition comprising:
    a vial having wall portions defining a chamber and an outlet communicating with said chamber, said wall portions being made of a polymeric material having a flexural modulus less than about 200,000 kg/cm$^2$;
    a photocurable material in said chamber, said material being dispensed through said outlet when said wall portions are squeezed together, said wall portions transmitting less than about 1.0% of actinic radiation, and wherein at least one of said wall portions transmits at least part of the visible spectrum; and
    an element in said chamber, said element having a density less than the density of said photocurable material in order to float in said photocurable material.

2. The packaged composition of claim 1, wherein said wall portions include a colorant.

3. The packaged composition of claim 1, wherein at least one of said wall portions includes a label.

4. The packaged composition of claim 1, wherein at least one of said wall portions is coated with a colorant.

5. The packaged composition of claim 1, wherein said photocurable material is selected from the group consisting of a dental adhesive, a dental primer, a dental luting cement, a dental crown build-up material and a dental sealant.

6. The packaged composition of claim 1, wherein said flexural modulus is less than about 2,000 kg/cm$^2$.

7. The packaged composition of claim 1, wherein said wall portions transmit less than about 0.5% of actinic radiation.

8. The packaged composition of claim 1, wherein said chamber has a certain height, and wherein said at least one of said wall portions that transmits at least part of the visible spectrum extends substantially along the entire height of said chamber.

9. A packaged composition comprising:

a vial having wall portions defining a chamber and an outlet communicating with said chamber;

a photocurable liquid in said chamber, said wall portions transmitting less than about 1.0% of actinic radiation, at least one of said wall portions transmitting at least part of the visible spectrum; and an element floating in said liquid, said element being visible through said at least one wall portion transmitting at least part of the visible spectrum in order to indicate the level of said liquid in said chamber.

10. The packaged composition of claim 9, wherein said element includes a hole extending through said element.

11. The packaged composition of claim 10, wherein said hole is located in a central region of said element.

12. The packaged composition of claim 9, wherein said wall portions transmit less than about 0.5% of actinic radiation.

13. The packaged composition of claim 9, wherein said photocurable liquid is selected from the group consisting of a dental adhesive, a dental primer, a dental luting cement, a dental crown build-up material and a dental sealant.

14. The packaged composition of claim 9, wherein said wall portions are made of a polymeric material having a flexural modulus less than about 20,000 kg/cm$^2$.

* * * * *